United States Patent [19]

Ison

[11] Patent Number: Plant 7,707

[45] Date of Patent: Nov. 12, 1991

[54] GRAPEVINE NAMED 'PAM'

[76] Inventor: William G. Ison, Rte. 1, Box 19, Hwy. 19, Brooks, Ga. 30205

[21] Appl. No.: 166,248

[22] Filed: Mar. 10, 1988

[51] Int. Cl.[5] ..... A01H 5/00

[52] U.S. Cl. ..... Plt./47

[58] Field of Search ..... Plt./47

*Primary Examiner*—Robert E. Bagwill

*Attorney, Agent, or Firm*—Eugene T. Holmes

[57] ABSTRACT

A cross between the female variety 5-11-3 and the pollen parent variety Senoia to produce an improved variety of muscadine grape.

1 Drawing Sheet

DESCRIPTION OF THE VARIETY

A cross between the seed variety 5-11-3 and the pollen parent Senoia variety.

The primary objective of the breeding was to produce an improved variety of the muscadine grape; the fruit of which would have superior characteristics than either parent. These characteristics include uniform ripening, high sugar content, large size, dry scar for longer shelf life, and the plant to be productive and vigorous.

In comparison to the seed parent, the new variety is larger and sweeter. The new variety resembles the seed parent in color; but resembles the pollen parent in vigor, productivity and dry scar. The fruit of the new variety contains on the average of from 21.50 to 22.50 percent soluble solids, which sugar content is higher than the sugar content of the fruit of either parent. The present variety yields on the average of 4 to 8 tons per acre in tests conducted at Ison's Nursery & Vineyards, Brooks, Ga. This new variety has very large fruit, extra long clusters, superior color, very good taste, and ripens mid-season.

Asexual reproduction of the new variety either by soft-wood cuttings or by layering as performed at Brooks, Ga. show that the above characteristics and distinctions are true to form and are established and transmitted through succeeding propagations.

The accompanying photograph shows a typical specimen of the vegetative growth and fruit of the new variety when the fruit is ripe and ready for picking. The color is as nearly true as reasonably possible to make the same in color illustrations of this character.

The following is a detailed description of the new variety.

Species: *Vitis rotundifolia.*
Type: Vine.
Seed Parent: 5-11-3.
Pollen Parent: Variety Senoia.

Propagation: Holds its characteristics through succeeding propagation by either layering or by soft-wood cuttings.
Locality where grown: Brooks, Ga.
Fruit borne: Usually in clusters of 6 to 18 berries per cluster.
Fruit size: Large, bigger than seed parent, $1\frac{1}{4}''$ diameter.
Fruit color: Greyed Yellow Group 160A Fan 4, The Royal Horticultural Society, London, England.
Sugar content: 21.50 to 22.50 percent soluble solids.
Fruit:
- *Shape.*—Round.
- *Seed.*—Average diameter $\frac{1}{8}''$, average seed per berry 2.65.
- *Pulp.*—Greyed Green Group, 195C Fan 4, The Royal Horticultural Society, London, England.
- *Consistency.*—Medium soft, medium juicy as compared to most muscadine vines.
- *Skin.*—Thick.

Foliage: Leaf Color Green Group, 13A Fan 3 The Royal Horticultural Society, London, England. Size and shape similar to most varieties.
Reproductive organs: Pistillate-not self-pollinating. Note: this is a female variety which can be reproduced from cuttings but when planted will not pollinate other varieties.
Canes: Medium to large.
Maturity date: Usually ripens about October 2 at Brooks, Ga.
Diseases: Tolerant to black rot and ripe rot and other muscadine diseases.
Growth habits: Vine vigorous and very productive, requires support.

This description was made from a muscadine vine grown at Ison's Nursery and Vineyards, Brooks, Ga. 30205.

I claim:

1. The new and distinct variety of the specified plant, as described and illustrated.

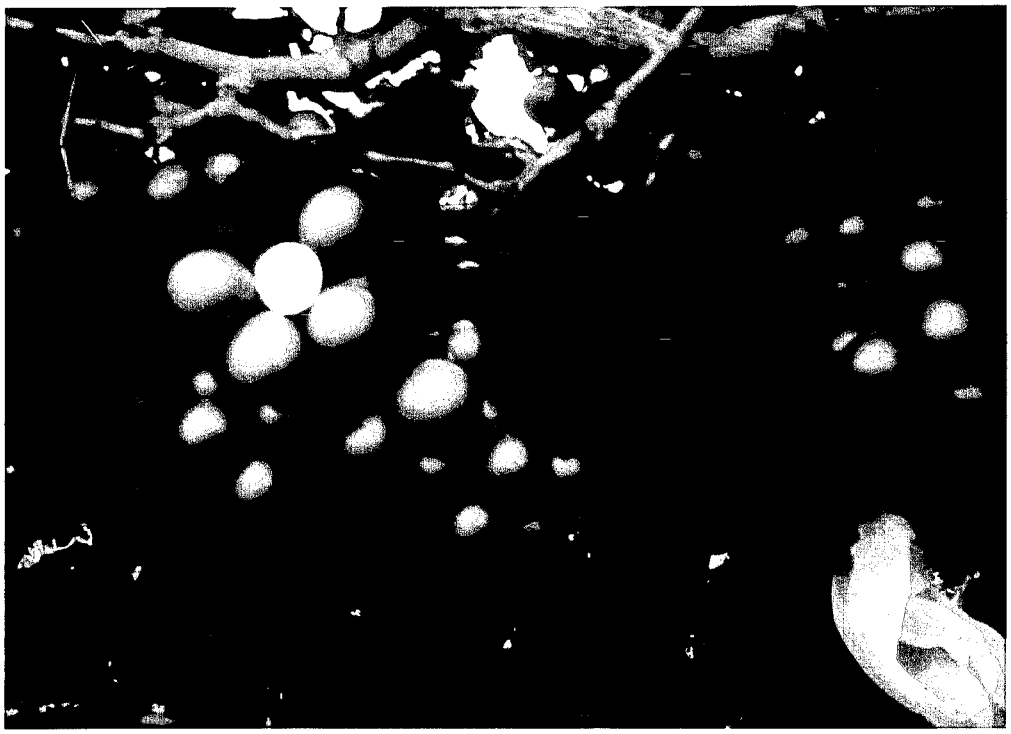

* * * * *